US009737385B1

(12) United States Patent
Kumar

(10) Patent No.: US 9,737,385 B1
(45) Date of Patent: Aug. 22, 2017

(54) BACKFLOW PREVENTER FOR SALIVA EJECTOR

(71) Applicant: Ajay Kumar, Palmdale, CA (US)

(72) Inventor: Ajay Kumar, Palmdale, CA (US)

( * ) Notice: Subject to any disclaimer, the term of this patent is extended or adjusted under 35 U.S.C. 154(b) by 49 days.

(21) Appl. No.: 14/740,886

(22) Filed: Jun. 16, 2015

(51) Int. Cl.
*A61C 17/14* (2006.01)
*A61C 17/06* (2006.01)
*A61B 5/117* (2016.01)

(52) U.S. Cl.
CPC .................. *A61C 17/043* (2013.01)

(58) Field of Classification Search
CPC ....... A61C 17/00; A61C 17/04–17/046; A61C 17/02–17/028; A61C 17/14
USPC ............................................. 433/91–96, 229
See application file for complete search history.

(56) References Cited

U.S. PATENT DOCUMENTS

| | | | | | |
|---|---|---|---|---|---|
| 2,529,499 | A | * | 11/1950 | Jankelson | A61C 17/043 15/421 |
| 2,574,135 | A | * | 11/1951 | Ward | A61C 17/043 433/96 |
| 3,092,910 | A | * | 6/1963 | Warriner | A61B 1/253 433/31 |
| 3,256,885 | A | * | 6/1966 | Higgins | A61C 17/043 433/91 |
| 3,541,583 | A | * | 11/1970 | Deuschle | A61C 17/043 433/96 |
| 3,570,525 | A | * | 3/1971 | Borsum | A61C 17/0202 137/320 |
| 4,049,000 | A | * | 9/1977 | Williams | A61M 1/0047 433/95 |
| 4,601,713 | A | * | 7/1986 | Fuqua | A61M 25/0023 604/103.14 |
| 4,608,017 | A | * | 8/1986 | Sadohara | A61O 5/40 433/81 |
| 4,684,345 | A | * | 8/1987 | Cattani | A61C 17/046 433/92 |
| 4,710,181 | A | * | 12/1987 | Fuqua | A61M 25/0023 604/103.05 |

(Continued)

OTHER PUBLICATIONS

Watson, C.M. et al., "Possibility of Cross-Contamination Between Dental Patients by Means of the Saliva Ejector," JADA, vol. 124, Apr. 1993, pp. 77-80.

(Continued)

*Primary Examiner* — Sundhara Ganesan
*Assistant Examiner* — Garrett Atkinson
(74) *Attorney, Agent, or Firm* — Innovation Capital Law Group, LLP; Vic Lin

(57) ABSTRACT

The system and method disclosed herein prevent a patient from interrupting the vacuum created by the vacuum line attached to the saliva ejector so that suction continues to be present even if the patient clamps his or her lips tightly about the shaft of the saliva ejector. In the illustrated embodiment, the backflow prevention mechanism includes a sleeve positionable on the shaft of the saliva ejector and engageable by the patient's lips. The sleeve includes at least one conduit that remains open to allow air to enter the patient's mouth even when the patient's lips are tightly closed. The air entering the patient's mouth via the at least one conduit enables the vacuum line to continue to draw bodily fluids and contaminants from the patient's mouth.

12 Claims, 9 Drawing Sheets

(56) References Cited

U.S. PATENT DOCUMENTS

| | | | | | |
|---|---|---|---|---|---|
| 5,013,300 | A | * | 5/1991 | Williams | A61M 1/008 433/91 |
| 5,195,952 | A | * | 3/1993 | Solnit | A61C 17/043 433/91 |
| 5,425,723 | A | * | 6/1995 | Wang | A61M 25/007 138/114 |
| 5,480,124 | A | * | 1/1996 | Bartlett | A61M 1/0043 251/304 |
| 5,509,802 | A | * | 4/1996 | Whitehouse | A61C 17/043 433/95 |
| 5,690,487 | A | * | 11/1997 | Whitehouse | A61C 17/043 433/91 |
| 5,704,785 | A | * | 1/1998 | Young | A61C 17/043 433/91 |
| 5,725,374 | A | * | 3/1998 | Young | A61C 17/04 433/95 |
| 5,728,078 | A | * | 3/1998 | Powers, Jr. | A61C 17/043 604/246 |
| 5,800,486 | A | * | 9/1998 | Thome | A61B 18/18 607/101 |
| 5,873,718 | A | * | 2/1999 | Sullivan | A61C 17/043 433/93 |
| 6,203,321 | B1 | * | 3/2001 | Helmer | A61C 17/04 433/95 |
| 6,602,072 | B2 | * | 8/2003 | Burney | A61C 17/043 433/96 |
| 7,131,839 | B2 | * | 11/2006 | March | A61C 17/043 433/91 |
| 7,335,023 | B2 | * | 2/2008 | Mahlmann | A61C 17/043 433/136 |
| 8,328,553 | B2 | * | 12/2012 | Broyles | A61C 9/0026 433/80 |
| 9,211,168 | B2 | * | 12/2015 | Broyles | A61C 9/0026 |
| 2003/0054317 | A1 | * | 3/2003 | Burney | A61C 17/043 433/96 |
| 2003/0219696 | A1 | * | 11/2003 | Moreland | A61C 17/043 433/95 |
| 2005/0175961 | A1 | * | 8/2005 | March | A61C 17/043 433/91 |
| 2006/0110702 | A1 | * | 5/2006 | Mahlmann | A61C 17/043 433/96 |
| 2006/0199147 | A1 | * | 9/2006 | Mahlmann | A61C 17/043 433/96 |
| 2006/0212056 | A1 | * | 9/2006 | Salvadori | A61C 3/00 606/167 |
| 2007/0105066 | A1 | * | 5/2007 | March | A61C 17/043 433/96 |
| 2008/0289696 | A1 | * | 11/2008 | Bushman | A61C 1/16 137/217 |
| 2009/0065067 | A1 | * | 3/2009 | Bushman | A61C 1/16 137/217 |
| 2009/0123886 | A1 | * | 5/2009 | Vaska | A61F 5/566 433/27 |
| 2009/0298010 | A1 | * | 12/2009 | Broyles | A61C 9/0026 433/90 |
| 2009/0317760 | A1 | * | 12/2009 | Gadbois | A61C 17/043 433/91 |
| 2010/0297577 | A1 | * | 11/2010 | Cohen | A61M 1/0056 433/92 |
| 2013/0040267 | A1 | * | 2/2013 | Bergheim | A61C 3/03 433/216 |
| 2013/0203012 | A1 | * | 8/2013 | Walker | A61C 17/043 433/92 |
| 2013/0337405 | A1 | * | 12/2013 | Anthony | A61C 17/043 433/91 |
| 2014/0322668 | A1 | * | 10/2014 | Chun | A61C 17/043 433/92 |
| 2015/0196375 | A1 | * | 7/2015 | Wegmann | A61C 17/043 433/92 |
| 2016/0038348 | A1 | * | 2/2016 | Booth | A61F 13/38 433/136 |

OTHER PUBLICATIONS

Mann, Ginger L. Byrd et al., "Backflow in Low-Volume Suction Lines: The Impact of Pressure Changes." JADA, vol. 127, May 1996, pp. 611-615.

Barbeau, J. et al. "Cross-contamination potential of saliva ejectors used in dentistry," Journal of Hospital Infection (1998) 40: 303-311.

Dickinson, Sharon K. et al., "Guidelines for Infection Control in Dental Health Care Settings," Crest® Oral-B® at dentalcare.com Continuing Education Course, Revised Jul. 19, 2013, 34 pages.

* cited by examiner

BACKFLOW PREVENTER FOR SALIVA EJECTOR

BACKGROUND OF THE INVENTION

Field of the Invention

This application is directed to dental accessories, and, more particularly, is directed to an apparatus and method for preventing backflow in saliva ejectors used for removing accumulated liquids and other materials from the mouth of a patient during dental procedures.

Description of the Related Art

A saliva ejector is an apparatus used by a dentist or a dental hygienist during dental procedures to evacuate saliva, blood and other debris from a patient's mouth. The saliva ejector includes a suction line and a low-volume saliva ejector tip. The saliva ejector tip is inserted into the patient's mouth with the ejector tip in the region of the material to be removed. Suction is applied via a suction line to evacuate the material from the patient's mouth and to discharge the evacuated material to a waste container. In accordance with acceptable dental practice, the saliva ejector tip is a single use device that is replaced after each patient. In contrast, the suction line may be replaced or cleaned only after the suction line has seen used with several patients. Unfortunately, this practice can result in fluids from a previous dental patient or from multiple previous patients remaining in the suction line when the saliva ejector is used on a subsequent patient.

A common dental practice is to have a patient close the patient's lips around the low-volume saliva ejector tip and expectorate to help evacuate the mouth. Closing the lips around the ejector tip can cause a decrease in the magnitude of the vacuum line negative pressure. The decrease in magnitude may allow the previously evacuated fluid remaining in the suction line to flow backwards into the patient's mouth. This backflow of fluid can carry oral contaminants such as blood, viruses, bacteria, and fungi from prior patients. Studies have found that oral bacteria can survive inside of the suction line. Furthermore, diseases, such as influenza, strep, and hepatitis B, can be passed to subsequent patients if material remaining in the suction line backflows into the patient's mouth.

In order to decrease the possibility of the backflow of fluids into a dental patient's mouth, dentists and hygienists routinely instruct patients not to close their lips around the saliva ejector tips so as to prevent a decrease in the negative magnitude of the vacuum line pressure. However, humans tend to close their lips around a straw when sucking, and the request to keep the lips apart during sucking is counter to this behavior. Moreover, even if a patient succeeds in overcoming the tendency to close his or her lips around the ejector tip, the saliva ejector tip may still get wedged in a position in the patient's mouth—for instance in the cheek folds—to block the end of the tip and cause a decrease in the negative magnitude of the vacuum line pressure, which can result in backflow.

Another approach for decreasing the chance of oral contaminants being passed from patient to patient is to clean or change the suction line after every patient. However, this approach is time consuming and is cost prohibitive. Furthermore, if the suction line is rinsed thoroughly with a germ killing rinse, any remaining rinse residue in the suction line may backflow into the mouth of a subsequent patient. This circumstance would be unpleasant for the dental patient or possibly dangerous depending on the caustic nature of the rinse.

It has been recognized in the art that cross-contamination between patients, for example, dental patients, can occur when evacuators (suctioning devices) attached to vacuum lines are used to remove such bodily fluids and contaminants. Various articles, guidelines and studies have addressed the potential for such cross-contamination including, for example: *Possibility of Cross-Contamination Between Dental Patients by Means of the Saliva Ejector*, C. M. Watson, R. L. S. Whitehouse, JADA, Vol. 124, April 1993; *Backflow in Low-Volume Suction Lines: The Impact of Pressure Changes*, G. Mann, T. Campbell and J. Crawford, JADA, Vol. 127, May 1996; *Cross-Contamination Potential of Saliva Ejectors Used in Dentistry*, J. Bargeau, et al., Journal of Hospital Infection, 1998: 40:303-11; and *Guidelines for Infection Control in the Dental Health Care Setting*—2003, Center for Disease Control, 2003, all of which are herein incorporated by reference to the extent not inconsistent with the present disclosure. Such cross-contamination can occur as vacuumed bodily fluids, contaminants or both can backflow from the vacuum line into the patient's mouth, body or both. Backflow can occur when flow is interrupted when a patient closes his or her mouth over the vacuum tip, thereby stopping flow or even overpowering the negative vacuum pressure by sucking on the tip.

SUMMARY OF THE INVENTION

In view of the foregoing, a need exists for a system and method that prevents backflow from a vacuum line attached to a saliva ejector, thus preventing vacuumed bodily fluids, contaminants or both from entering the patient's mouth via the saliva ejector. The system and method disclosed herein prevent a patient from interrupting the vacuum created by the vacuum line attached to the saliva ejector so that suction continues to be present even if the patient clamps his or her lips tightly about the shaft of the saliva ejector. Accordingly, the system and method accommodate the natural tendency of a patient to close his or her lips during the suction procedure. In the illustrated embodiment, the backflow prevention mechanism includes a sleeve positionable on the shaft of the saliva ejector and engageable by the patient's lips. The sleeve includes at least one conduit that remains open to allow air to enter the patient's mouth even when the patient's lips are tightly closed. The air entering the patient's mouth via the at least one conduit enables the vacuum line to continue to draw bodily fluids and contaminants from the patient's mouth.

One aspect of the embodiments disclosed herein is a backflow preventer for a saliva ejector wherein the saliva ejector includes a shaft having a distal end and a proximal end, wherein the distal end is configured to receive fluids, and wherein the proximal end connectable to a vacuum line. The backflow preventer comprises a hollow cylindrical shaft extending longitudinally between a first end surface and a second end surface. The hollow cylindrical shaft has an inner surface and an outer surface with a shaft wall defined between the inner surface and the outer surface. The inner surface is configured to fit over and frictionally engage the shaft of the saliva ejector. At least one longitudinal bore extends through the shaft wall between the first end surface and the second surface to provide a passageway for air.

In certain embodiments of the backflow preventer, the inner surface of the hollow cylindrical shaft has a shape approximating an ellipse. The ellipse has a major axis and a minor axis, wherein the major axis has a length greater than an outside diameter of the shaft of the saliva ejector, and the minor axis has a length less than the outside diameter of the shaft of the saliva ejector. The hollow cylindrical shaft is deformable by pressure applied across the major axis to temporarily decrease the length of the major axis of the ellipse while increasing the length of the minor axis of the ellipse such that the length of the minor axis is greater than the outside diameter of the shaft of the saliva ejector to enable the hollow cylindrical shaft to be positioned on the shaft of the saliva ejector.

In certain embodiments of the backflow preventer, the inner surface of the hollow cylindrical shaft of the backflow preventer includes a first indentation aligned with a first end of the minor axis and a second indention aligned with a second end of the minor axis. The indentions reduce the thickness of the wall of the hollow cylindrical shaft at the first and second ends of the minor axis to facilitate the outward deformation of the wall.

In certain embodiments of the backflow preventer, the inner surface of the hollow cylindrical shaft has a primary shape approximating a circle. The circle has a diameter greater than an outside diameter of the shaft of the saliva ejector. The inner surface further includes a plurality of protrusions extending inward from the primary shape of the inner surface. The protrusions have innermost surfaces that define an inner circle having a diameter less than the outside diameter of the shaft of the saliva ejector. The innermost surfaces frictionally engage the shaft of the saliva ejector when the backflow hollow cylindrical shaft is positioned on the saliva ejector.

In certain embodiments of the backflow preventer, a metallic wire is embedded in the wall of the backflow preventer. The metallic wire retains a shape when bent such that when the backflow preventer is bent to a selected shape the metallic wire inhibits the backflow preventer from returning to a previous shape.

Another aspect of the embodiments disclosed herein is a method for preventing backflow through a saliva ejector when a patient's lips are closed onto the saliva ejector. The method comprises positioning a backflow preventer onto a shaft of the saliva ejector. The backflow preventer includes at least one airflow passage between a first end surface and a second end surface. The method further comprises positioning the saliva ejector in the patient's oral cavity. The backflow preventer is positioned on the saliva ejector at a location between the patient's lips such that when the patient's lips are closed, the first end surface of the backflow preventer is exposed to the ambient atmosphere outside the patient's lips and the second end surface of the backflow preventer is located within the oral cavity of the patient. The at least one airflow passage enables air to pass from the ambient atmosphere into the oral cavity of the patient.

In certain embodiments, the method further comprises bending a portion of the saliva ejector and the backflow preventer from an original longitudinal shape to a selected arcuate shape. The backflow preventer includes an embedded metallic wire which inhibits the backflow prevent from returning to the original longitudinal shape.

BRIEF DESCRIPTION OF THE DRAWINGS

The foregoing aspects and other aspects of this disclosure are described in detail below in connection with the accompanying drawing figures in which.

DETAILED DESCRIPTION OF PREFERRED EMBODIMENTS

An anti-suction saliva ejector is disclosed in the attached drawings and is described below. The embodiment is disclosed for illustration of the anti-suction saliva ejector and is not limiting except as defined in the appended claims.

Figure 1:
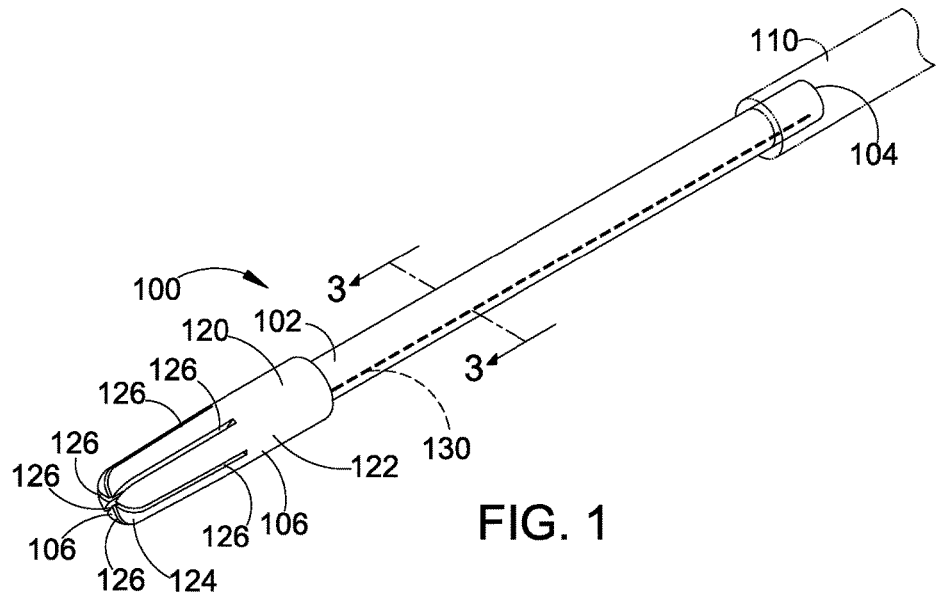
FIG. 1 illustrates a perspective view of a saliva ejector onto which the backflow preventer disclosed herein can be installed.
Figure 2:
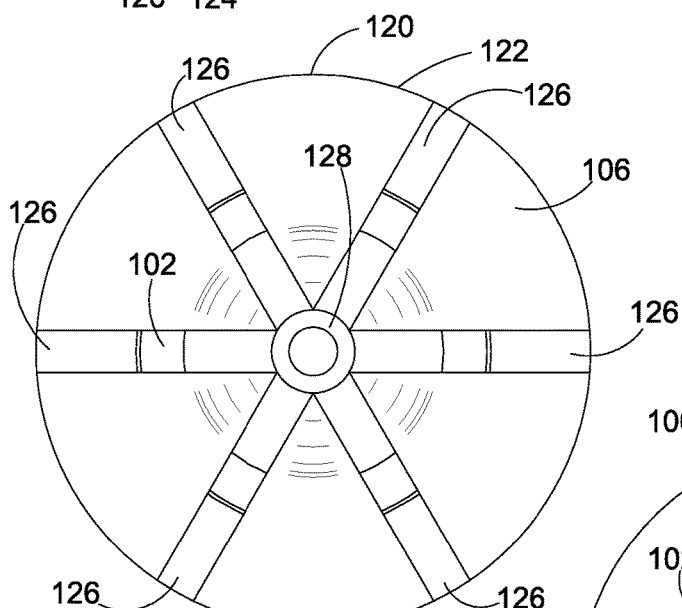
FIG. 2 illustrates a distal end elevational view of the saliva ejector of FIG. 1.
Figure 3:
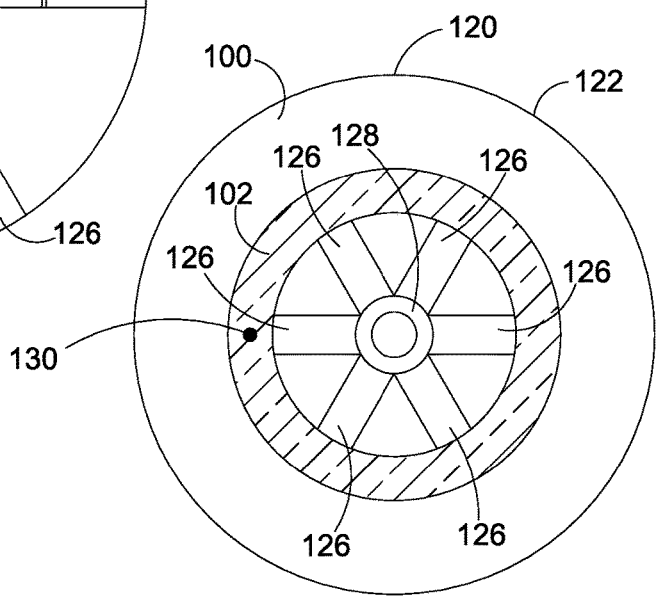
FIG. 3 illustrates a cross-sectional elevational view taken from the proximal end of the saliva ejector along the line 3-3 of FIG. 1.

FIGS. 1, 2 and 3 illustrate an example of a typical saliva ejector 100. As illustrated, the saliva ejector comprises a hollow cylindrical shaft 102 having an open proximal end 104 and having a suction head 106 at the opposite distal end. As used herein, "proximal" refers to the end of the saliva ejector closest to the dentist, the dental hygienist or other dental practitioner (not shown) handling the saliva ejector, and "distal" refers to the opposing end, which is inserted into the mount of a patient (see FIGS. 4 and 5 discussed below).

The shaft 102 of the saliva ejector 100 has a typical outside diameter of approximately 6.5 millimeters (slightly more than ¼ inch). The proximal end 104 of the saliva ejector is attachable to a vacuum line 110 in a conventional manner. For example, the vacuum line can comprise medical grade tubing having an inside diameter of approximately ¼ inch so that the vacuum line fits snugly onto the shaft. The vacuum line is coupled to a vacuum source (not shown). The vacuum source applies a vacuum to the saliva ejector via the vacuum line and receives the bodily fluids, rinse water and other materials suctioned from a patient's mouth.

The suction head 106 at the distal end of the hollow shaft 102 typically comprises an enlarged cap 120. The cap has a collar 122 that attaches the cap to the shaft. The cap also has an inlet portion 124. The inlet portion can have many different configurations. In the illustrated saliva ejector, the inlet portion includes a plurality of longitudinal slots 126 that extend from the distal end of the cap to the collar. An internal support ring 128 keeps the material of the cap surrounding the slots spaced apart to prevent the slots from closing. Fluids and contaminants pass through the slots and are drawn through the hollow shaft to the vacuum line 110.

The hollow shaft 102 of the typical saliva ejector 100 is flexible and can be bent to a desired configuration. The shaft can comprise medical grade thermoplastic or other suitable material. Such a material tends to return to an original shape after being bent (e.g., to the generally straight shape illustrated in FIGS. 1-3). Accordingly, many saliva ejectors include a longitudinal shape-retention wire (e.g., a copper wire) 130 (shown in hidden lines in the figures) that retains a shape into which it is bent.

Figure 4:
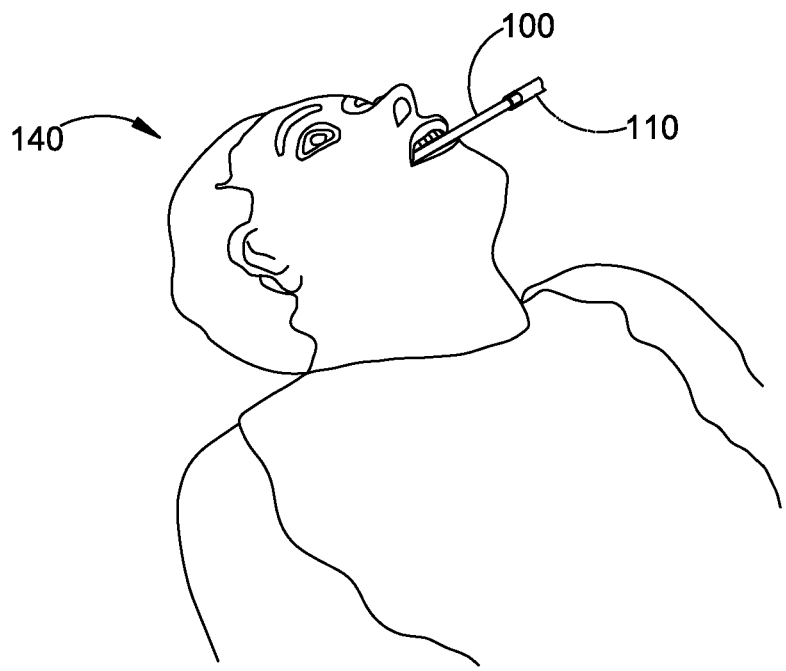
FIG. 4 illustrates a pictorial perspective view of the saliva ejector of FIG. 1 with the proximal end of the saliva ejector attached to a vacuum line and with a distal end portion of the saliva ejector inserted into the mouth of a patient, the patient's lips shown in the preferred open position.

As shown in FIG. 4, while performing a dental procedure, a dental practitioner (e.g., a dentist, a dental hygienist, or the like) frequently inserts the saliva ejector 100 into the mouth of a patient 140 to remove bodily fluids and contaminated material. The saliva ejector can remain in the original straight configuration and be held in the mouth by the dental practitioner during the suction procedure as shown in FIG. 4. Alternatively, the saliva ejector may be bent into a hook-like configuration so that the saliva ejector can remain in the mouth for an extended period without being held. Often, the insertion of the saliva ejector is accompanied by spraying of water (not shown) into the mouth to dislodge contaminated material so that the material and the water can be suctioned from the mouth.

Figure 5:
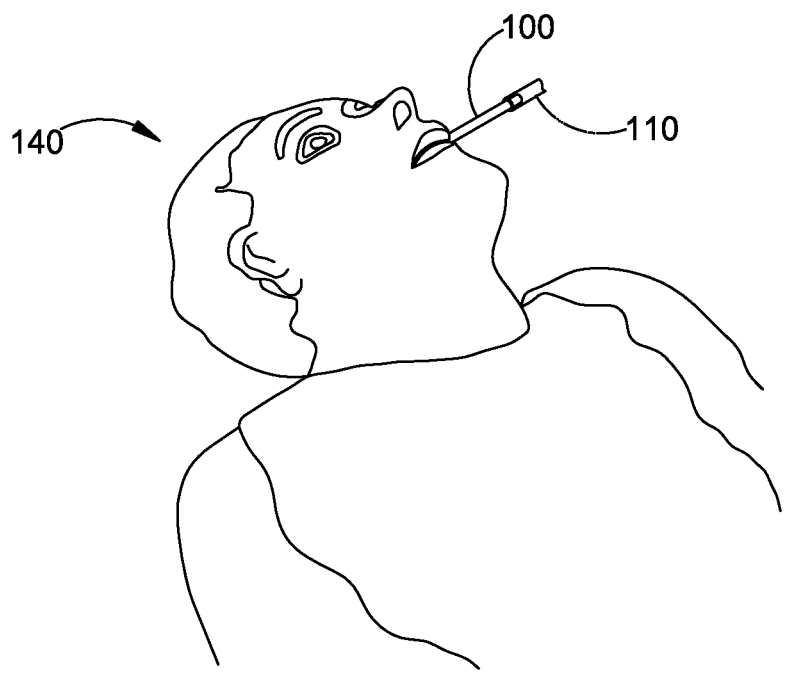
FIG. 5 illustrates the pictorial perspective view of FIG. 4 with the patient's lips closed around the shaft of the saliva ejector.

Although the patient 140 should be instructed to keep his or her mouth open during the suction procedure as shown in FIG. 4, the appropriate instructions are often not provided, or, if provided, the instructions are ignored by the patient. Thus, many, if not most, patients close their lips around the shaft of the saliva ejector 100 as illustrated in FIG. 5. As discussed above, when a patient closes his or her lips around the shaft of the saliva ejector, a vacuum quickly forms in the patient's mouth, which counteracts the vacuum provided by the vacuum line 110. Backflow can occur, which can result into bodily fluids and other materials in the vacuum line flowing from the vacuum line into the patient's mouth. Such fluids or other materials can be from a previous patient, can be residual cleaning fluids from attempts to clean the vacuum line after a previous patient procedure or can be a combination of both. Such a backflow of material is undesirable at best and can be dangerous, as discussed above.

Figure 6:
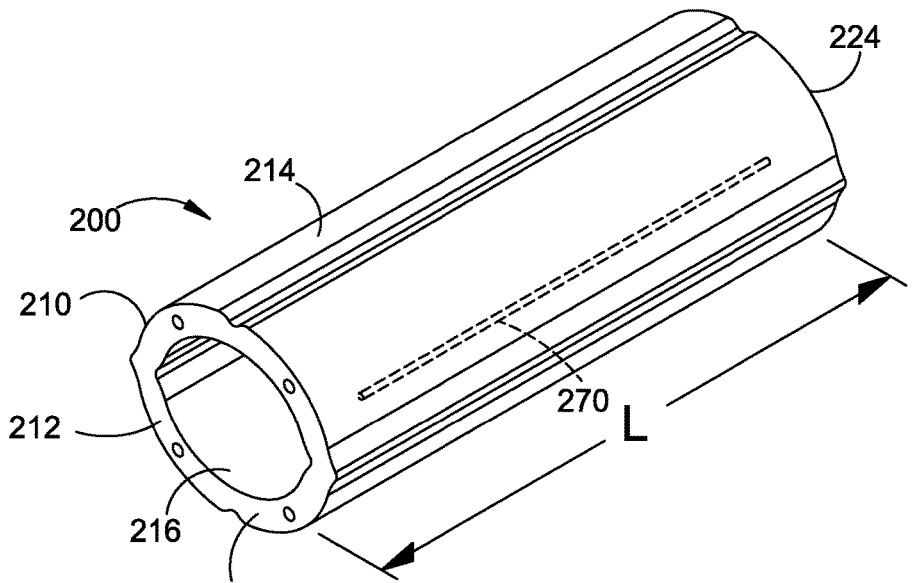
FIG. 6 illustrates a perspective view of a first embodiment of a backflow preventer, the embodiment including an internal shape-retention wire shown in hidden lines.
Figure 7:
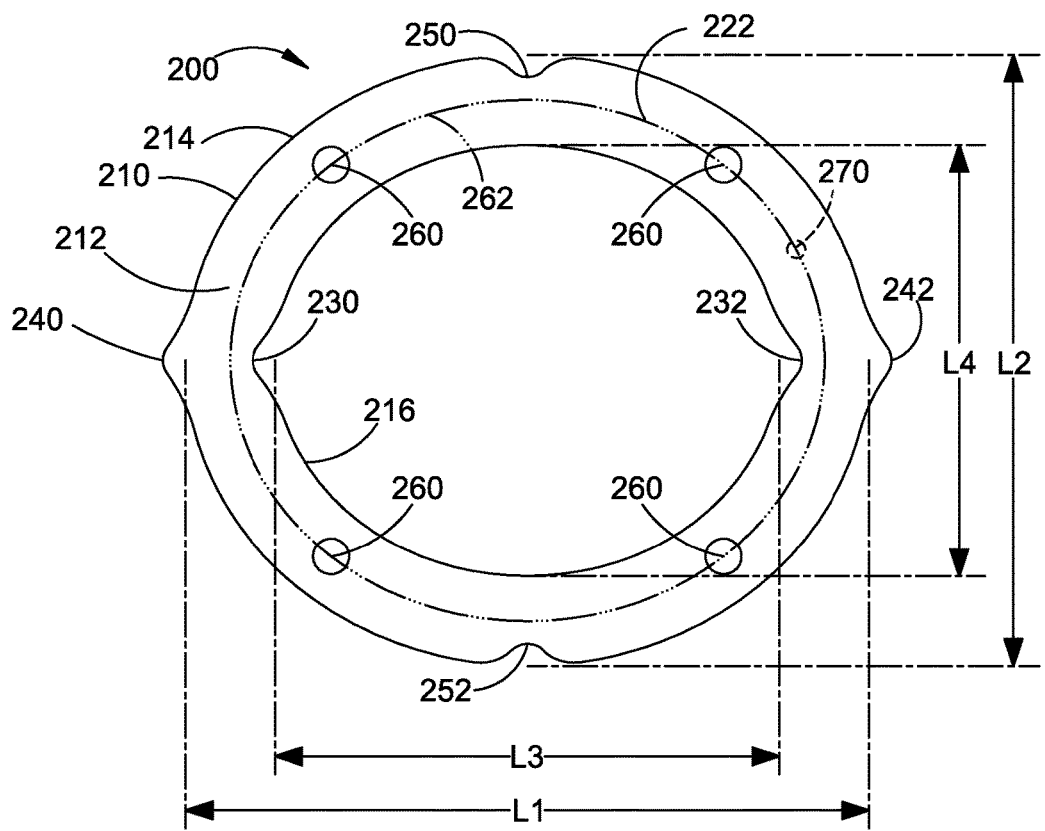
FIG. 7 illustrates a distal end view of the backflow preventer of FIG. 6.

FIG. 6 illustrates a perspective view of a backflow preventer 200 in accordance with a first embodiment. The backflow preventer solves the backflow problem discussed above. FIG. 7 illustrates an end view of the backflow preventer. The backflow preventer comprises a hollow cylinder 210 having a wall 212 with a generally elliptical cross-sectional profile. The cylinder may be referred to as an elliptic cylinder wherein the wall has an outer surface 214 and an inner surface 216. In the illustrated embodiment, the cylinder has a length L (FIG. 6) from a first end surface 220 to a second end surface 222. In the illustrated embodiment, the length L is approximately 1 inch. The length L can vary. For example, in alternative embodiments, the length L can be as short as 0.5 inch and can be as long as 4 inches depending on the application. For example, a shorter length can be used for a pediatric patient, and a longer length can be used when the saliva ejector 100 is likely to be moved to multiple locations within a patient's mouth (e.g., during a typical tooth cleaning procedure). In the illustrated embodiment, the backflow preventer is extruded from a medical grade thermoplastic elastomer, such as, for example, the material used in medical tubing and the like.

As illustrated in FIG. 7, the outer surface 214 of the generally elliptical cross-sectional profile of the cylinder wall 212 of the cylinder 210 of the backflow preventer 200 has an outer major axis (horizontal in FIG. 7) with a length L1 of approximately 0.38 inch and has an outer minor axis (vertical in FIG. 7) with a length L2 of approximately 0.34 inch; however, the profile is modified as described below. The primary thickness of the wall of the cylinder between the outer surface and the inner surface 216 is approximately 0.05 inch; however, the thickness of the wall varies at specific locations as described below. The primary thickness of the wall can also differ for different embodiments. For example, the wall thickness of 0.05 inch may be suitable for most applications; however, a greater wall thickness can be advantageous in other applications. The generally elliptical cross-sectional profile of the inner surface 216 of the cylinder wall has an inner major axis (horizontal in FIG. 7) with a length L3 of approximately 0.28 inch and has an inner minor axis (vertical in FIG. 7) with a length L4 of approximately 0.24 inch. The foregoing dimensions of the inner and outer axes are referred to herein as the "resting dimensions" of the backflow preventer.

As further illustrated in FIG. 7, the inner surface 216 of the wall 212 of the cylinder 210 includes a first inner arcuate notch 230 and a second inner arcuate notch 232 positioned at opposite ends of the inner major axis. Each inner arcuate notch has a radius of approximately 0.025 inch; and each inner arcuate notch includes a pair of fillets to the inner surface, each fillet having a radius of approximately 0.1 inch.

As further illustrated in FIG. 7, the outer surface 214 of the wall 212 of the cylinder 210 includes a first arcuate protrusion 240 and a second arcuate protrusion 242 at opposite ends of the outer major axis. Each protrusion has a radius of approximately 0.025 inch; and each protrusion includes a pair of fillets to the outer surface, each fillet having a radius of approximately 0.1 inch. As illustrated the protrusions on the outer surface are aligned with the inner arcuate notches.

The outer surface 214 of the wall 212 further includes a first outer arcuate notch 250 and a second outer arcuate notch 252 at opposite ends of the outer minor axis. Each outer arcuate notch has a radius of approximately 0.025 inch; and each outer arcuate notch includes a pair of fillets to the outer surface, each fillet having a radius of approximately 0.025 inch. The two outer arcuate notches cause the wall to be thinner between the inner surface 216 and the notches. As described below, the two outer arcuate notches provide a hinging effect that is used to enable the backflow preventer to be installed easily onto the shaft 110 of the saliva ejector 100 shown in FIGS. 1-3.

The wall 212 of the cylinder 210 further includes a plurality of longitudinal bores 260 that extend from the first end surface 220 to the second end surface 222. In the illustrated embodiment, each longitudinal bore has a diameter of approximately 0.02 inch. In alternative embodiments, the bores may have different diameters. In the illustrated embodiment, four longitudinal bores are provided; and the four bores are spaced apart from the respective major and minor axes by approximately 45 degrees. Preferably, each bore is positioned approximately midway between the outer surface 214 and the inner surface 216. For example, in the illustrated embodiment, the bores are positioned on an elliptical curve 262 (shown in phantom) having a major axis with a length of approximately 0.37 inch and having a minor axis with a length of approximately 0.33 inch.

As further shown in FIGS. 6 and 7, the backflow preventer 200 can also include an encapsulated wire 270 (shown in hidden lines) in the wall 212 of the cylinder. The encapsulated wire extends generally between the first end 220 and the second end 222 of the cylinder; however, in the illustrated embodiment, the encapsulated wire is molded into the wall of the backflow preventer and is not exposed at either end of the backflow preventer. In one embodiment, the wire has a diameter of approximately 0.01 inch (e.g., approximately 30 AWG (American wire gauge)) and comprises copper or other suitable metal. The location of the encapsulated wire within the wall is not critical. In the illustrated embodiment, the wire is located approximately midway between the outer surface 214 and the inner surface 216 and is located approximately midway between one of the longitudinal bores 260 and the arcuate protrusion 240. The encapsulated wire functions as a shape-retention wire so that the backflow preventer will remain bent if the dental practitioner bends the backflow preventer and the saliva ejector 100 as part of a dental procedure.

Figure 9:
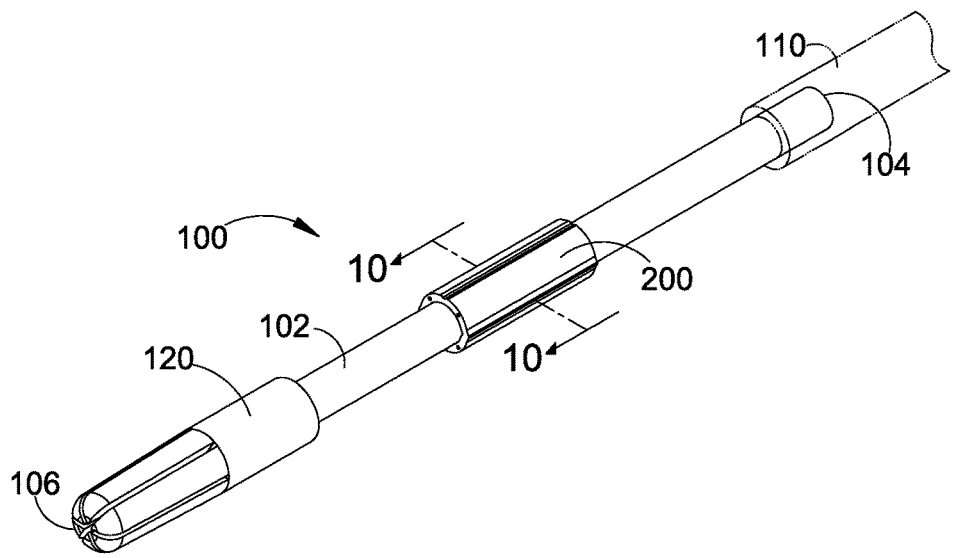
FIG. 9 illustrates a perspective view of the backflow preventer of FIGS. 6-8 attached to the shaft of the saliva ejector of FIGS. 1-3.

The inner arcuate notches 230, 232, the outer arcuate notches 250, 252 and the protrusions 240, 242 on the inner surface 214 and the outer surface 216 of the wall 212 of the cylinder 210 enable the dental practitioner to attach the backflow preventer 200 to the shaft 102 of the saliva ejector 100 as shown in FIG. 9 and to move the backflow preventer to a desired position on the shaft of the saliva ejector.

Figure 8:
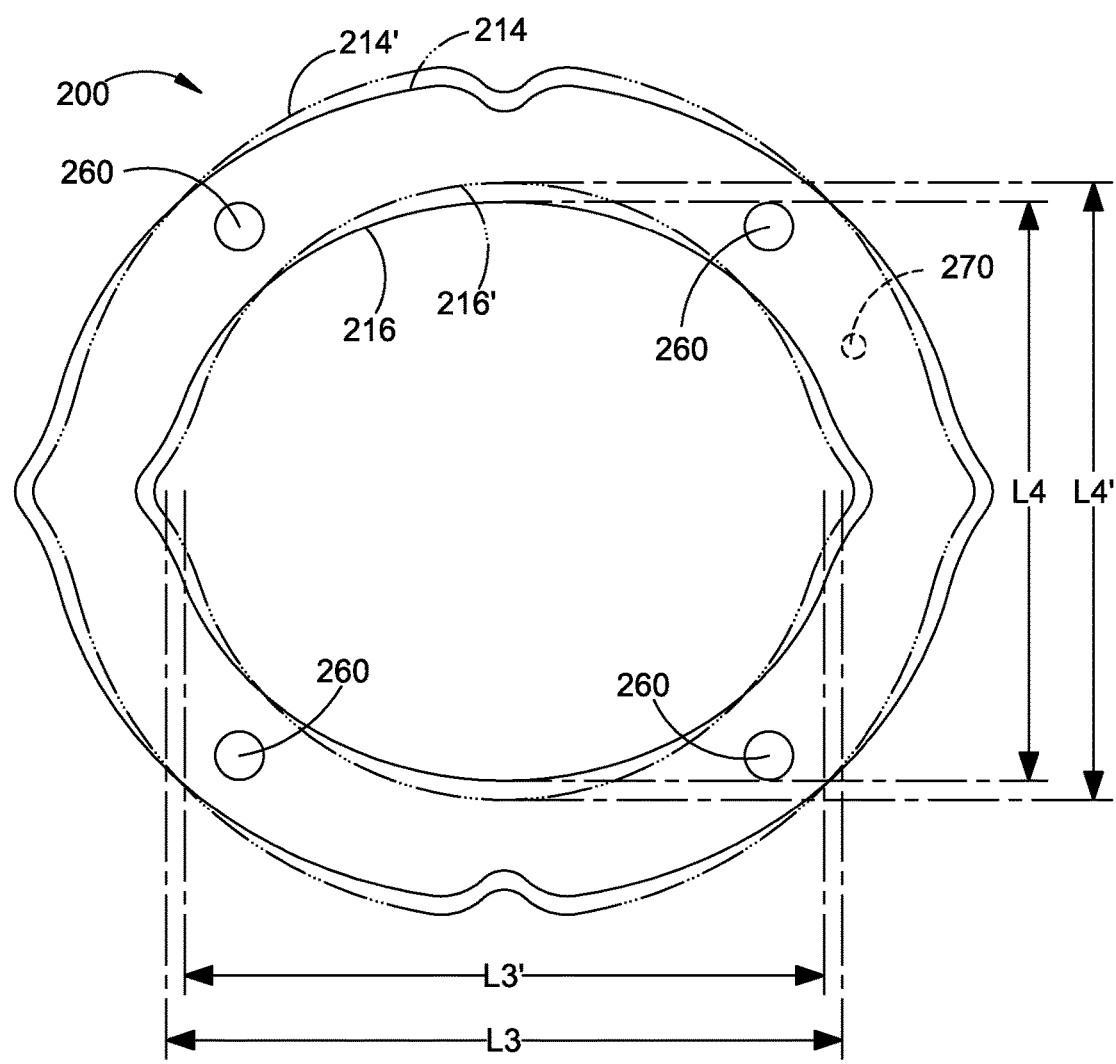
FIG. 8 illustrates the distal end view of the backflow preventer of FIG. 7 with the relaxed configuration of FIG. 7 shown in solid lines and with the squeezed (vertically stretched) configuration shown in phantom lines.

In the illustrated embodiment, the inner minor axis length L4 of the wall 212 of the cylinder 210 is approximately 0.24 inch, which is slightly less than the outer diameter of the shaft 102 of the saliva ejector 100. Thus, the backflow preventer cannot be easily inserted onto the shaft of the saliva ejector in view of the resting dimensions of the backflow preventer. As illustrated in FIG. 8, by applying pressure to the first protrusion 240 and the second protrusion 242 of the backflow preventer, the dental practitioner causes the wall of the cylinder to be squeezed inwardly along the inner major axis L3 and the outer major axis L1 to shorten the two major axes. The shortening along the major axes is represented by the shortening of the inner major axis from the length L3 to the length L3'. The hinging effect of the thinner thicknesses of the wall between the inner surface 216 of the wall and each of the outer arcuate notches 250, 252 causes a portion of the wall proximate to the outer arcuate notches to bulge outwardly, which causes the lengths of the minor axes to increase while the pressure is applied. The lengthening of the minor axes is represented in FIG. 8 by the increase in the length of the inner minor axis from L4 to L4'. Accordingly, the notches facilitate the deformation of the wall of the cylinder outward along the minor axes and inward along the major axes as illustrated by the modified inner surface 216' and the modified outer surface 214', which are shown in phantom lines in FIG. 8. The increase in length of the inner minor axis from L4 to L4' is sufficient to cause the inner minor axis length to temporarily exceed the 6.5-millimeter outer diameter of the shaft of the saliva ejector. Although the applied pressure also causes the inner major axis length to decrease from L3 to L3', the original inner major axis length (resting dimension) of approximately 0.28 inch is sufficient so that the reduced length L3' while the pressure is applied remains greater than the outer diameter of the shaft of the saliva ejector. Thus, the dental practitioner is able to easily slide the backflow preventer onto the shaft of the saliva ejector and to move the backflow preventer to a desired location on the shaft as shown in FIGS. 9 and 10.

After positioning the backflow preventer 200 on the saliva ejector 100, the pressure applied to the protrusions 240, 242 is released so that the backflow preventer relaxes toward the original shape; however, the complete relaxation of the backflow preventer is precluded because the outer diameter of the shaft 102 of the saliva ejector is greater than the original length L4 of the inner minor axis. Thus, the inner surface 216 of the backflow preventer engages the shaft as shown in the end view of FIG. 10. The engagement of the inner surface of the backflow preventer with the shaft provides sufficient friction with respect to the shaft to inhibit longitudinal movement of backflow preventer along the shaft so that the backflow preventer remains where positioned by the dental practitioner. The backflow preventer may be repositioned by applying pressure to the protrusions as before or by applying sufficient pressure overcome the frictional engagement of the inner wall with the shaft.

Figure 10:
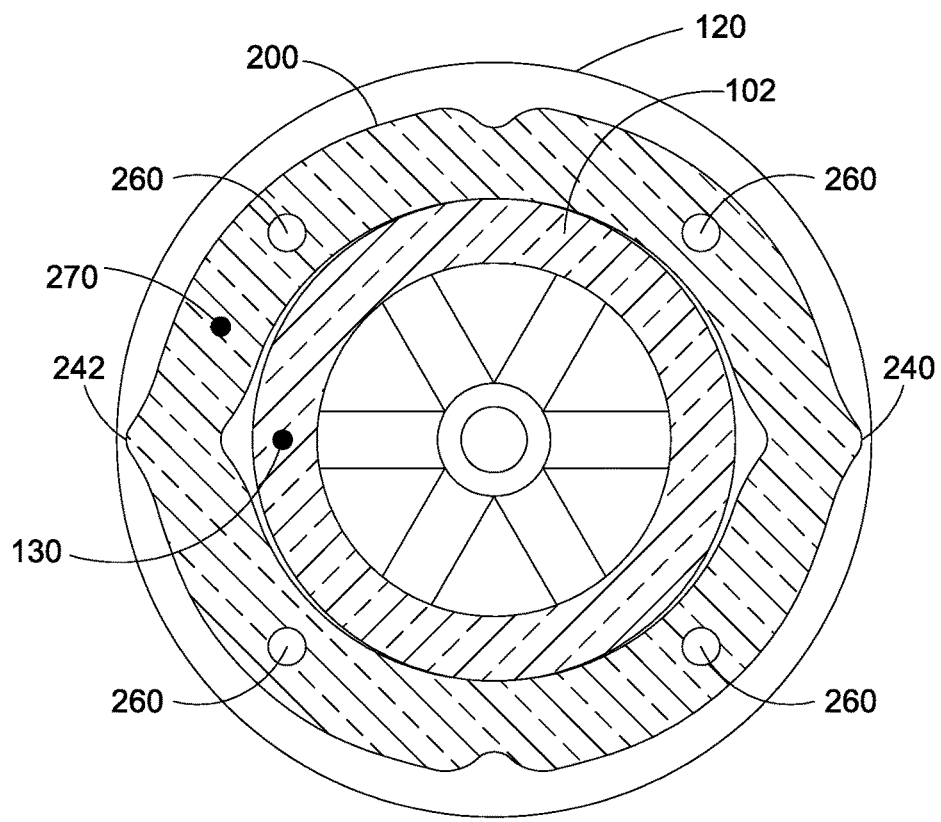
FIG. 10 illustrates a cross-sectional elevational view of the saliva ejector and the backflow preventer of FIG. 9 taken from the proximal end of the saliva ejector along the line 10-10 of FIG. 9.
Figure 11:
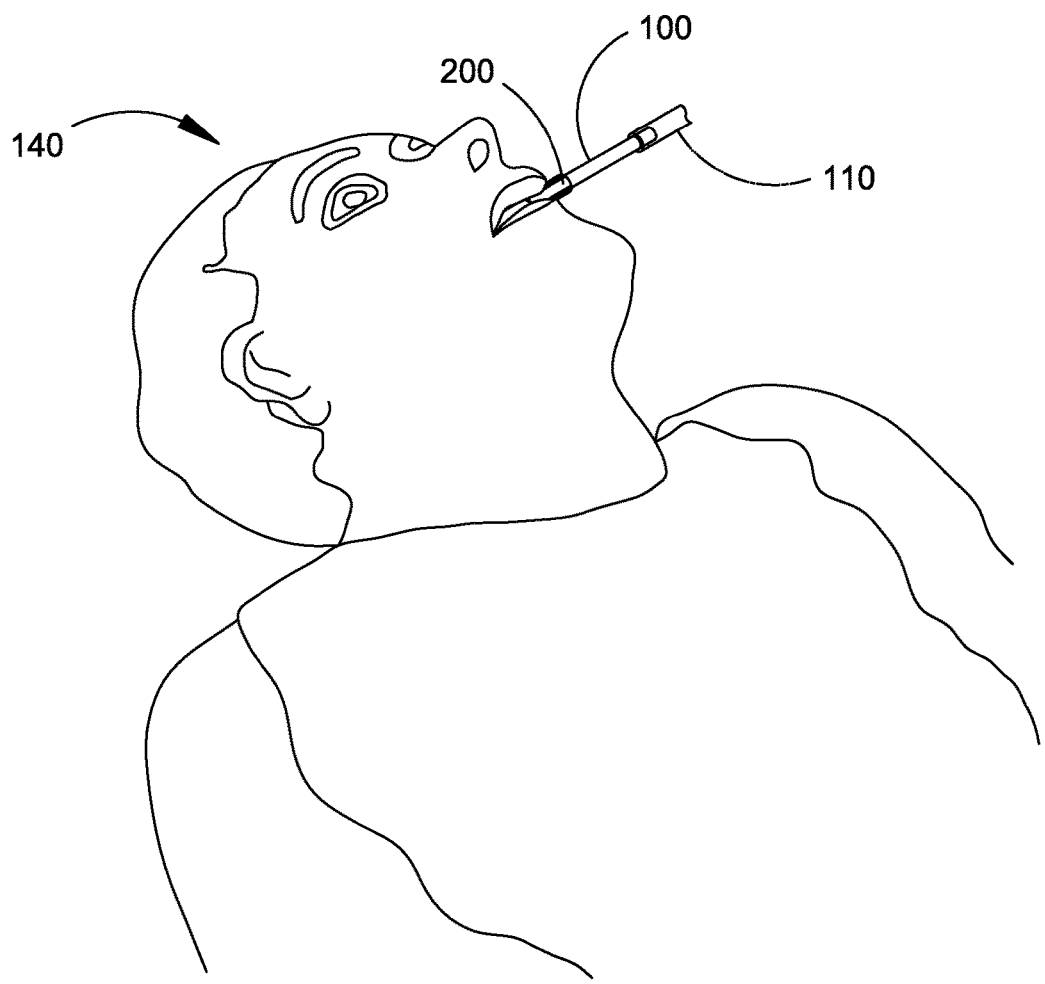
FIG. 11 illustrates a pictorial perspective view of the backflow preventer and saliva ejector of FIGS. 9 and 10 with a distal end portion (not shown) of the saliva ejector in the patient's mouth and with the backflow preventer between the patient's lips.

After installing the backflow preventer 200 onto the saliva ejector 100 as shown in FIGS. 9 and 10, the vacuum line 110 is attached to the shaft 102 of the saliva ejector in a conventional manner, as described above. The backflow preventer is positioned on the shaft of the saliva ejector so that when the saliva ejector is placed in the mouth of the patient 140, the backflow preventer is located between the lips of the patient as shown in FIG. 11. Thus, even if the patient closes his or her lips onto the shaft of the saliva ejector as shown in FIG. 11, the backflow preventer will be positioned between the lips with one end surface (e.g., first end surface 220) exposed outside the patient's lips and with the other surface (e.g., the second end surface 222) positioned within the patient's mouth. Thus, the plurality of longitudinal bores 260 provide open conduits for the passage of air from outside the patient's lips to inside the patient's mouth even if the lips are closed tightly around the outer surface 214 of the backflow preventer. Additional air flow can also be provided in the cavities created between outer wall of the shaft of the saliva ejector and the first and second inner arcuate notches 230, 232.

If the initial positioning of the backflow preventer 200 on the saliva ejector 100 is not correct, the backflow preventer is easily repositioned by applying pressure to the protrusions 240, 242 to temporarily increase the inner minor axis length L4, by moving the backflow preventer while the pressure is applied, and then by releasing the pressure to again engage the outer surface of the shaft 102 of the saliva ejector. The backflow preventer may also be repositioned in a similar manner if the location of the saliva ejector is changed during the procedure, and the original positioning of the backflow preventer is no longer correct.

As discussed above, the shaft 102 of the saliva ejector 100 may be bent to a hook-like shape or other suitable shape to allow the saliva ejector to remain within the mouth of the patient 140 for a longer duration. If the backflow preventer 200 is positioned on the portion of the shaft to be bent, the backflow preventer is sufficiently flexible to also be bent. As further discussed above, the backflow preventer can also include the encapsulated wire 270 to assist in retaining the bent shape of the backflow preventer so that the resilient thermoplastic material of the backflow preventer does not tend to straighten, which could result in modifying the desired hook-like shape of the shaft of the saliva ejector.

After the backflow preventer 200 is installed on the saliva ejector 100 and the saliva ejector is connected to the vacuum line 110, the saliva ejector is positioned (and repositioned, if necessary) in the mouth of the patient 140 with the backflow preventer between the patient's lips as shown in FIG. 11. During the dental procedures, the saliva ejector is operated by the dental practitioner in a conventional manner by selectively activating the vacuum source when evacuation is needed. Even if the patient closes his or her lips over the saliva ejector, the backflow preventer between the patient's lips maintains open air passages via the longitudinal bores 260 that prevent a vacuum from forming within the oral cavity of the patient's mouth. Thus, vacuum applied via the vacuum line continues to remove fluids and other material from the mouth without any occurrence of backflow. In general, the first end (distal end) surface 222 of the backflow preventer is located a sufficient distance from the portion of the patient's mouth where the saliva and other debris collect so that the saliva and other debris do not enter the longitudinal bores during the evacuation process.

Figure 12:
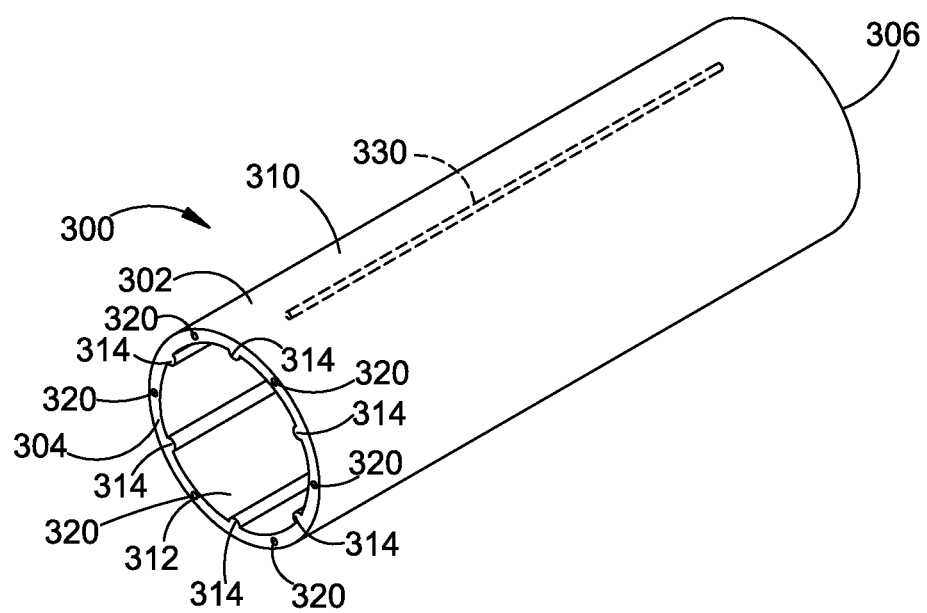
FIG. 12 illustrates a perspective view of a second embodiment of a backflow preventer, the second embodiment including a shape-retention wire shown in hidden lines.

FIG. 12 illustrates a perspective view of a backflow preventer 300 in accordance with a second embodiment. The structure of the second backflow preventer is similar to the structure of the previously described backflow preventer and operates in a similar manner. The second backflow preventer comprises a hollow cylinder 302, which can have a length from a first end surface 304 to a second end surface 306 that can be varied in accordance with the application, as discussed above. In the illustrated embodiment, the length can vary from approximately 0.5 inch to approximately 4 inches.

Figure 13:
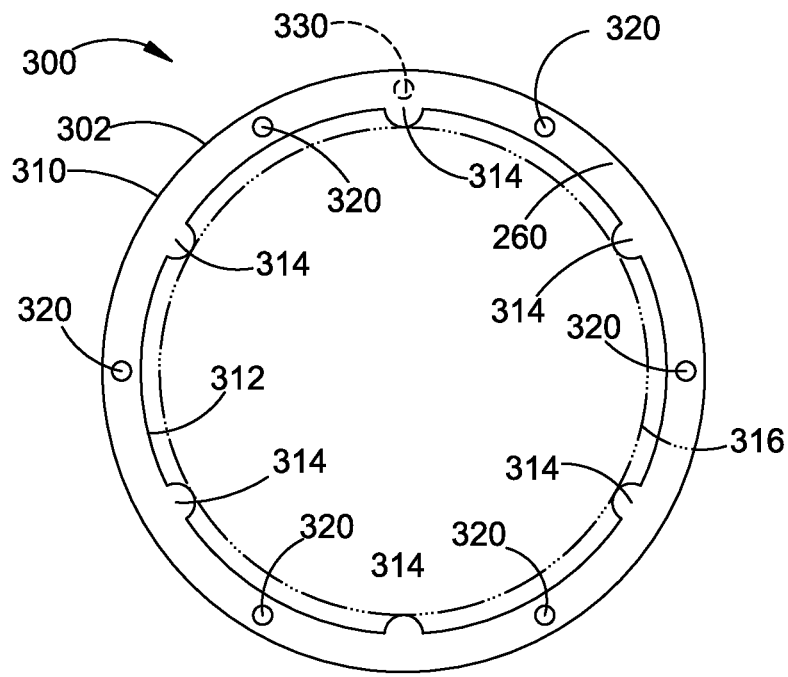
FIG. 13 illustrates a distal end view of the backflow preventer of FIG. 12.
Figure 14:
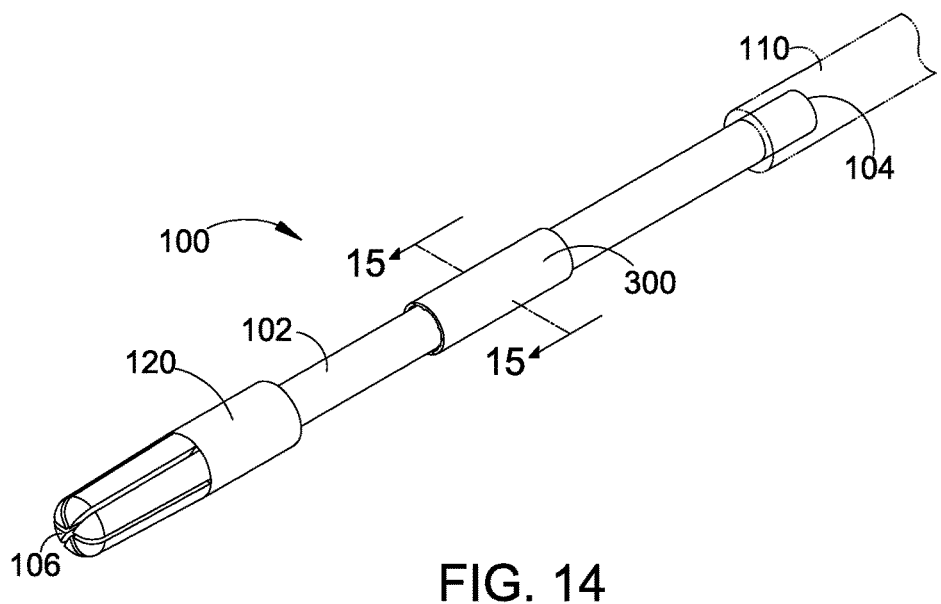
FIG. 14 illustrates a perspective view of the backflow preventer of FIGS. 12 and 13 installed on the saliva ejector of FIGS. 1-3.
Figure 15:
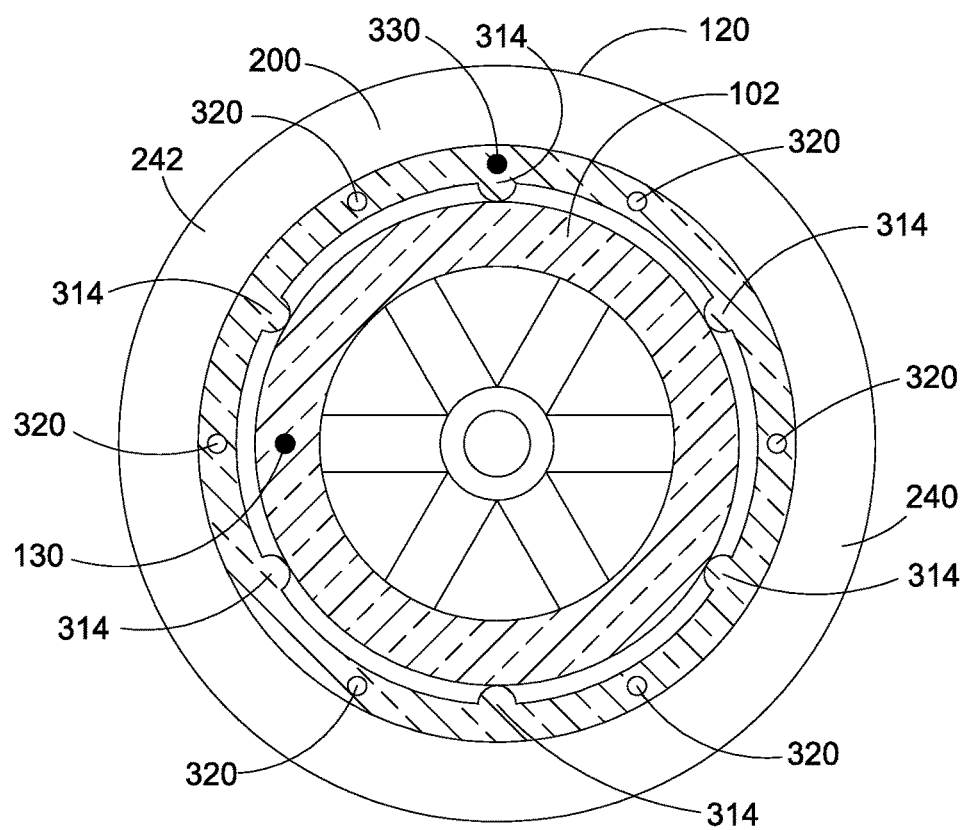
FIG. 15 illustrates a cross-sectional elevational view of the saliva ejector and the backflow preventer of FIG. 14 taken from the proximal end of the saliva ejector along the line 15-15 of FIG. 14.

Unlike the previously described backflow preventer 200 with the elliptical cross-sectional profile, the second backflow preventer 300 of FIG. 11 has a generally circular profile as shown in FIG. 13. An outer surface 310 of the hollow cylinder 302 has an outer diameter in a range of approximately 0.28 inch to approximately 0.3 inch. The second backflow preventer has an inner surface 312 having a primary inner diameter of approximately 0.26 inch; however, the inner surface includes a plurality of arcuate crush ribs (or inward protrusions) 314. In the illustrated embodiment, six crush ribs are positioned at approximately equal angular distances around the inner surface of the backflow preventer (e.g., at approximately 60-degree intervals. The crush ribs extend inwardly from the inner surface by a distance of approximately 0.01 to 0.02 inch such that the inner surface has a secondary inner diameter (represented by a circle 316 in phantom) of slightly less than 0.25 inch. Accordingly, the selected secondary inner diameter provides a snug fit against the outer surface of the shaft 102 of the saliva ejector 100 when positioned on the saliva ejector as shown in FIGS. 14 and 15. The arcuate crush ribs provide longitudinal contact surfaces where the innermost surfaces of the crush ribs are tangential to the outer surface of the shaft. Accordingly, the crush ribs provide sufficient frictional engagement with the outer surface of the shaft so that the alternative backflow preventer will remain where positioned; however, the frictional engagement is easily overcome by applying moderate force to slide the backflow preventer to a desired location on the shaft as described above.

The second backflow preventer 300 of FIGS. 12 and 13 includes a plurality of longitudinal bores 320 which extend from the first end surface 304 to the second end surface 306 of the hollow cylinder 302. In the illustrated embodiment, six longitudinal bores are positioned equally distantly around the cylinder. Each bore is generally positioned midway between adjacent crush ribs 314 and is generally positioned midway between the outer surface 310 and the primary inner surface 312. In the illustrated embodiment, each of the longitudinal bores has a diameter of approximately 0.01 inch. The diameter is sufficiently large to allow air to flow therethrough to preclude the formation of a vacuum as described above. The diameter is sufficiently small to inhibit the outward flow of saliva and other fluids which may be close to the second end surface of the backflow preventer. For example, the surface tension of the saliva is sufficiently high to prevent the saliva from entering the small diameter longitudinal bores. When positioned on the shaft 102 of the saliva ejector 100 as shown in FIGS. 14 and 15, the spacing between the primary inner surface and the shaft between adjacent crush ribs also provides longitudinal pathways for additional air flow into a patient's mouth.

The alternative backflow preventer 300 of FIGS. 13 and 13 may also include an encapsulated wire 330, which operates as described above to assist in retaining a bent shape of the combined backflow preventer and saliva ejector 100.

Figure 16:
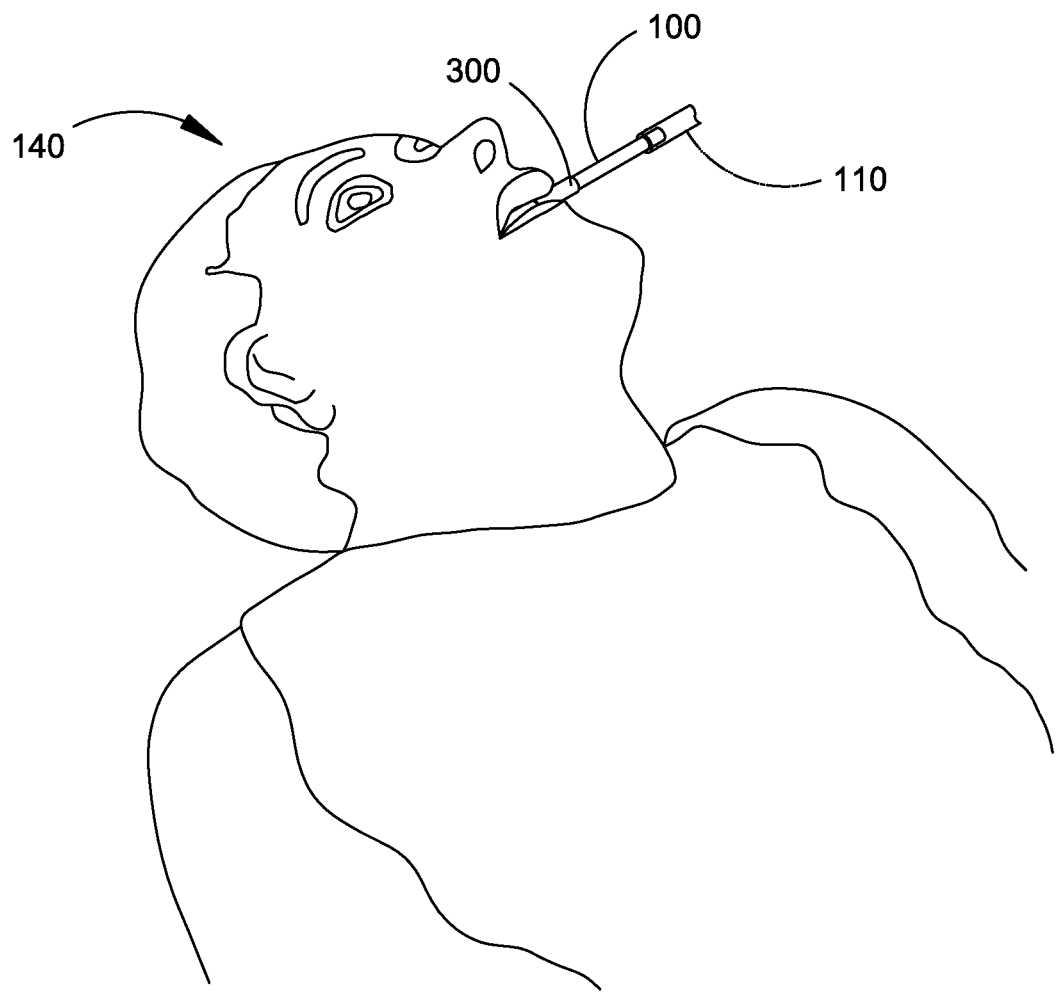
FIG. 16 illustrates a pictorial perspective view of the backflow preventer and saliva ejector of FIG. 14 with a distal end portion (not shown) of the saliva ejector positioned in a patient's mouth and with the backflow preventer between the patient's lips.

As illustrated in FIG. 16, the second backflow preventer 300 and the saliva ejector 100 operate in a similar manner to the previously described combination of the first backflow preventer 200 and the saliva ejector. When the second backflow preventer and the saliva ejector are positioned in the mouth of the patient 140, the second backflow preventer is positioned (or repositioned if necessary) on the saliva ejector so that the second backflow preventer is positioned between the patient's lips as shown in FIG. 16 with the first (distal) end surface 304 in the patient's oral cavity and with the second (proximal) end surface 306 exposed to the ambient atmosphere. Thus, even if the patient's lips are closed around the outer surface of the backflow preventer, air will pass through the longitudinal bores 320 to prevent a vacuum from forming within the oral cavity.

One skilled in art will appreciate that the foregoing embodiments are illustrative of the present invention. The present invention can be advantageously incorporated into alternative embodiments while remaining within the spirit and scope of the present invention, as defined by the appended claims.

What is claimed is:

1. A backflow preventer apparatus comprising a backflow preventer and a saliva ejector, the saliva ejector including a shaft having a distal end and a proximal end, wherein the distal end is configured to receive fluids and the proximal end is connectable to a vacuum line, the backflow preventer comprising:

a hollow cylindrical shaft extending longitudinally between a first end surface and a second end surface, the hollow cylindrical shaft having an inner surface and an outer surface with a shaft wall defined between the inner surface and the outer surface, the inner surface configured to fit over and frictionally engage the shaft of the saliva ejector such that the backflow preventer is configured for sliding movement along the length of the shaft of the saliva ejector; and at least one longitudinal bore surrounded by and extending through the shaft wall between the first end surface and the second surface to provide a passageway for air.

2. The backflow preventer apparatus as defined in claim 1, wherein the inner surface of the hollow cylindrical shaft has a shape approximating an ellipse, the ellipse having a major axis and a minor axis, the major axis having a length greater than an outside diameter of the shaft of the saliva ejector, the minor axis having a length less than the outside diameter of the shaft of the saliva ejector, the hollow cylindrical shaft deformable by pressure applied across the major axis to temporarily decrease the length of the major axis of the ellipse while increasing the length of the minor axis of the ellipse such that the length of the minor axis is greater than the outside diameter of the shaft of the saliva ejector to enable the hollow cylindrical shaft to be positioned on the shaft of the saliva ejector.

3. The backflow preventer apparatus as defined in claim 2, wherein the inner surface of the hollow cylindrical shaft of the backflow preventer includes a first indentation aligned with a first end of the minor axis and a second indention aligned with a second end of the minor axis, the indentions reducing the thickness of the wall of the hollow cylindrical shaft at the first and second ends of the minor axis to facilitate the outward deformation of the wall.

4. The backflow preventer apparatus as defined in claim 1, wherein the inner surface of the hollow cylindrical shaft has a primary shape approximating a circle, the circle having a diameter greater than an outside diameter of the shaft of the saliva ejector, the inner surface further including a plurality of protrusions extending inward from the primary shape of the inner surface, the protrusions having innermost surfaces that define an inner circle having a diameter less than the outside diameter of the shaft of the saliva ejector, the innermost surfaces frictionally engaging the shaft of the saliva ejector when the backflow hollow cylindrical shaft is positioned on the saliva ejector.

5. The backflow preventer apparatus as defined in claim 1, further comprising a metallic wire embedded in the wall of the backflow preventer, the metallic wire retaining a shape when bent such that when the backflow preventer is bent to a selected shape the metallic wire inhibits the backflow preventer from returning to a previous shape.

6. A method for preventing backflow through a saliva ejector when a patient's lips are closed onto the saliva ejector, the method comprising:
  positioning a backflow preventer onto a shaft of the saliva ejector, the backflow preventer including at least one airflow passage between a first end surface and a second end surface, wherein the backflow preventer is positioned such that the shaft of the saliva ejector extends beyond the first end surface and the second end surface thereof; and
  positioning the saliva ejector in the patient's oral cavity, the backflow preventer positioned on the saliva ejector at a location between the patient's lips such that when the patient's lips are closed, the first end surface of the backflow preventer is exposed to the ambient atmosphere outside the patient's lips and the second end surface of the backflow preventer is located within the oral cavity of the patient, the at least one airflow passage enabling air to pass from the ambient atmosphere into the oral cavity of the patient.

7. The method for preventing backflow as defined in claim 6, further comprising bending a portion of the saliva ejector and the backflow preventer from an original longitudinal shape to a selected arcuate shape, the backflow preventer including an embedded metallic wire which inhibits the backflow prevent from returning to the original longitudinal shape.

8. A backflow preventer apparatus comprising a backflow preventer and a saliva ejector, the saliva ejector including a shaft having a distal end and a proximal end, wherein the distal end is configured to receive fluids and the proximal end is connectable to a vacuum line, the backflow preventer comprising:
  a hollow cylindrical shaft extending longitudinally between a first end surface and a second end surface, the hollow cylindrical shaft having an inner surface and an outer surface with a shaft wall defined between the inner surface and the outer surface, the inner surface configured to fit over and frictionally engage the shaft of the saliva ejector such that the backflow preventer is configured for sliding movement along the length of the shaft of the saliva ejector; and
  at least one longitudinal bore extending through the shaft wall between the first end surface and the second surface to provide a passageway for air, wherein
  the backflow preventer is positionable such that the shaft of the saliva ejector extends beyond both the first and second end surface of the hollow cylindrical shaft of the backflow preventer.

9. The backflow preventer apparatus as defined in claim 8, wherein the inner surface of the hollow cylindrical shaft has a shape approximating an ellipse, the ellipse having a major axis and a minor axis, the major axis having a length greater than an outside diameter of the shaft of the saliva ejector, the minor axis having a length less than the outside diameter of the shaft of the saliva ejector, the hollow cylindrical shaft deformable by pressure applied across the major axis to temporarily decrease the length of the major axis of the ellipse while increasing the length of the minor axis of the ellipse such that the length of the minor axis is greater than the outside diameter of the shaft of the saliva ejector to enable the hollow cylindrical shaft to be positioned on the shaft of the saliva ejector.

10. The backflow preventer apparatus as defined in claim 8, wherein the inner surface of the hollow cylindrical shaft of the backflow preventer includes a first indentation aligned with a first end of the minor axis and a second indention aligned with a second end of the minor axis, the indentions reducing the thickness of the wall of the hollow cylindrical shaft at the first and second ends of the minor axis to facilitate the outward deformation of the wall.

11. The backflow preventer apparatus as defined in claim 8, wherein the inner surface of the hollow cylindrical shaft has a primary shape approximating a circle, the circle having a diameter greater than an outside diameter of the shaft of the saliva ejector, the inner surface further including a plurality of protrusions extending inward from the primary shape of the inner surface, the protrusions having innermost surfaces that define an inner circle having a diameter less than the outside diameter of the shaft of the saliva ejector, the innermost surfaces frictionally engaging the shaft of the saliva ejector when the backflow hollow cylindrical shaft is positioned on the saliva ejector.

12. The backflow preventer apparatus as defined in claim 8, further comprising a metallic wire embedded in the wall of the backflow preventer, the metallic wire retaining a shape when bent such that when the backflow preventer is bent to a selected shape the metallic wire inhibits the backflow preventer from returning to a previous shape.

\* \* \* \* \*